United States Patent [19]
Haley et al.

[11] Patent Number: 5,169,777
[45] Date of Patent: Dec. 8, 1992

[54] COMPOSITION OF BIOLOGICALLY PURE CULTURES OF ALCALIGENES DENITRIFICANS DENITRIFICANS AND A POROUS CARRIER USEFUL FOR BIODEGRADATION

[75] Inventors: Mark V. Haley, Jarretsville, Md.; Wayne G. Landis, Bellingham, Wash.

[73] Assignee: The United States of America as represented by the Secretary of the Army, Washington, D.C.

[21] Appl. No.: 573,970

[22] Filed: Aug. 27, 1990

Related U.S. Application Data

[62] Division of Ser. No. 429,299, Oct. 27, 1989, Pat. No. 4,965,202.

[51] Int. Cl.⁵ .............................................. C12R 1/05
[52] U.S. Cl. .................... 435/252.1; 435/128; 435/170; 435/176; 435/177; 435/262; 435/829
[58] Field of Search .............. 435/128, 170, 176, 177, 435/252.1, 262, 829

[56] References Cited

U.S. PATENT DOCUMENTS

| | | | |
|---|---|---|---|
| 4,304,590 | 12/1981 | Grade et al. | 514/673 |
| 4,427,435 | 1/1984 | Lorenz et al. | 514/214 |
| 4,752,318 | 6/1988 | Lorenz et al. | 514/643 |
| 4,804,629 | 2/1989 | Roy | 435/262 |
| 4,833,086 | 5/1989 | Horowitz | 435/262 |
| 4,965,202 | 10/1990 | Haley et al. | 435/170 |

*Primary Examiner*—Herbert J. Lilling
*Attorney, Agent, or Firm*—Anthony T. Lane; Edward Goldberg; Edward F. Costigan

[57] ABSTRACT

The present invention is a process of degrading 1,4-dibenz-oxazepine with a microorganism enzymatically capable of converting the 1,4-dibenz-oxazepine into at least o-nitrophenol which is further converted to catechol. The present invention is preferably carried out using a strain of *Alcaligenes denitrificans denitrificans*. Additional related compounds which can be degraded with *Alcaligenes denitrificans denitrificans* include: o-nitrophenol, catechol, and 3-methylcatechol.

3 Claims, 3 Drawing Sheets

COMPOSITION OF BIOLOGICALLY PURE CULTURES OF ALCALIGENES DENITRIFICANS DENITRIFICANS AND A POROUS CARRIER USEFUL FOR BIODEGRADATION

This application is a division of Ser. No. 07/429,299, filed Oct. 27, 1989, now U.S. Pat. No. 4,965,202.

The present invention relates to the biodegradation of 1,4-dibenz-oxazepine and related compounds; and more particularly to the degradation of such compounds with the bacteria *Alcaligenes denitrificans denitrificans.*

BACKGROUND OF THE INVENTION

One of the largest problems facing our society today is the growing accumulation of hazardous waste. Private industry as well as government agencies are under strict compliance to the Resource Conservation and Recovery Act and Regulations. Processes are needed which can reduce or eliminate hazardous waste on site.

Biodegradation through the use of microorganisms is one option which has great potential for reducing stock piles of hazardous waste as well as lowering toxicity.

Organisms reduce the effects of toxic materials through detoxification mechanisms. The classic case of such an enzymatic system in aquatic organisms are the phylogenetically wide spread glutathione S-transferases. These enzymes have the ability to conjugate and subsequently detoxify a wide variety of substrates. Reference is made to J. Stenersen and N. Oien, *Comp. Biochem. Physiol.*, Vol. 69, 1981, pp. 243-252; Y. C., Awasthi, D. D. Dao, and R. P. Saneto, *Biochem. J.*, Vol. 191, 1980 pp. 1-10; W. B. Jakoby, W. B., *Adv. Enzymol*, Vol. 46, 1978, pp. 383-414; and G. A. LeBlanc, and B. J. Cochrane, *Comp. Biochem. Physiol.*, Vol. 82C, 1985, pp. 37-42.

Monoxygenase systems are responsible for the biotransformation of a variety of compounds. (Lech, J. J. and Vodicnik, M. J., *Fundamentals of Aquatic Toxicology*, Eds. Rand, G. M. and Petrocelli, S. R., Hemisphere Publishing Corporation, New York, 1985, pp. 526-557). A wide range of microbes degrade a variety of xenobiotics both aerobically and anaerobically.

The exploitation of microbial and molecular biology for the clean up of hazardous wastes has been extensively discussed. Reference is made to G. S. Omen and A. Hollaender, *Genetic Control of Environmental Pollutants*, Plenum Press, New York, pp. 408, 1984; and G. S. Omen, *Environmental Biotechnology: Reducing Risks from Environmental Chemicals through Biotechnology*, Plenum Press, New York, 1988, pp. 505. Some success has been realized in the biorestoration of aquifers contaminated with organic compounds as disclosed by M. D. Lee, J. M. Thomas, R. C. Borden, P. B. Bedient, C. H. Ward and J. T. Wilson, in *Critical Reviews in Environmental Control*, Vol. 18, 1988, pp. 29-89. Currently, a great deal of research is being conducted into optimizing conditions for biodegradation in bioreactors and in situ. Reference is made to M. A. Bianchi, R. J. Portier, K. Fujisaki, C. B. Henry, P. H. Templet and J. E. Matthews, *Aquatic Toxicology and Hazard Assessment*, 10 Volume, ASTM STP 971. W. J. Adams, G. A. Chapman and W. G. Landis, Eds. *American Society for Testing and Materials*, 1988, pp. 503-527. Pentachlorophenol removal from soil and groundwater using both a Flavobacterium strain and adapted consortia has been disclosed. (R. L. Crawford and W. W. Mohn, *Enzyme Microb. Technol.*, Vol. 7, 1985, pp. 617-620; E. J. Brown, J. J. Pignatello, M. M. Martinson and R. L. Crawford, *Appl. and Environmental Microbiology*, Vol. 52, 1986, pp. 92-97; D. L. Saber and R. L. Crawford, *Appl. and Environmental Microbiology*, Vol. 1985, pp. 1512-1518; and J. G. Steiert and R. L. Crawford, *Trends in Biotechnology*, Vol. 3, 1985, pp. 300-305). These developments are critical to the way aquatic toxicologists view the effects and fate of xenobiotics and the techniques for restoration of contaminated sites.

Members of the genus Alcaligenes have been isolated from both terrestrial and aquatic environments. There have been cases of Alcaligenes being isolated from various human body fluids such as blood, urine, and spine (K. Kerster and J. DeLey, *Bergey's Manual of Systematic Bacteriology*, Vol. 1, Eds. N. E. Krieg and J. G. Holt, Williams and Wilkins, Baltimore, Md., 1984, pp. 361-373). Apparently the genus of gram negative bacteria is widespread and versatile in xenobiotic metabolism.

Alcaligenes strains have been reported for use to degrade various organic materials. A marine strain of Alcaligenes has been reported to degrade biphenyl and methylbyphenyl components of crude oil, but not n-alkanes. Reference is made to P. M. Fedorak and W. S. Westlake, *Can. J. Microbiol.*, Vol. 29, 1983, pp. 497-503. However, *Alcaligenes odorans* DSM 30033 has been reported to degrade indole and related ringed organics. Reference is made to G. Claus and H. J. Kutzer, *System Appl. Microbiol.*, Vol. 4, 1983, pp. 169-180. Polychlorinated biphenyl has been reported to be degraded by Alcaligenes strain Y42 in K. Furukawa, F. Matsumura and K. Tonomura, *Agric. Biol. Chem.*, Vol. 42, 1978, pp. 543-548. The PCB, $^{14}D$-2,5,2'-trichlorobiphenyl, was absorbed into the cell surface and then gradually metabolized. Meta cleavage products were reported using thin layer chromatography, however neither $^{14}C$-metabolites nor $^{14}CO_2$ was observed. Anaerobic benzoate catabolism for Alcaligenes is mediated by the plasmid pCBI as disclosed by C. K. Blake and G. D. Hegeman, *J. Bacteriology*, Vol. 169, 1987, pp. 4878-4883. The plasmid is 17.4 kbp and is self transmissible to Psuedomonas species. Another plasmid, pJP4, confers upon its host *Alcaligenes eutrophus* JMP134(pJP4) the ability to use 3-chlorobenzoate or 2,4-dichlorophenoxyacetic acid (2,4-D) as sole carbon sources. Reference is made to R. H. Don, A. J. Weightman, H. J. Knackmuss and K. N. Timmis, *J. Bacteriology*, Vol. 161, 1985, pp. 85-90. Plasmid pJP4 is 75 kbp in size and contains five genes coding for the catabolic pathways.

1,4-dibenz-oxazepine is a material which is useful for riot control. However, it is extremely recalcitrant to degradation, and is highly toxic to several aquatic organisms. The degradation of 1,4-dibenz-oxazepine and related compounds both in a bioreactor and in situ is desirable.

SUMMARY OF THE INVENTION

The present invention is a process of degrading 1,4-dibenz-oxazepine with a microorganism enzymatically capable of degrading the 1,4-dibenz-oxazepine.

The present invention includes a process of degrading 1,4-dibenz-oxazepine with a strain of *Alcaligenes denitrificans denitrificans*. Additional compounds which can be degraded with *Alcaligenes denitrificans denitrificans* include: O-nitrophenol, catechol, and 3-methylcatechol.

A strain of *Alcaligenes denitrificans denitrificans*, identified as CR-1, which is useful in the process of the present invention has been selected which can resist 1,4-dibenz-oxazepine concentrations of up to at least 200 mg/L and is capable of survival in an aquatic ecosystem.

CR-1, and compositions comprising CR-1, are useful to degrade 1,4-dibenz-oxazepine in the environment and in bioreactors.

The process and composition of the present invention allows normally recalcitrant 1,4-dibenz-oxazepine to be biologically degraded to less toxic products which can be more easily discarded, recycled, or eliminated.

DESCRIPTION OF THE PREFERRED EMBODIMENTS

Figure 1:
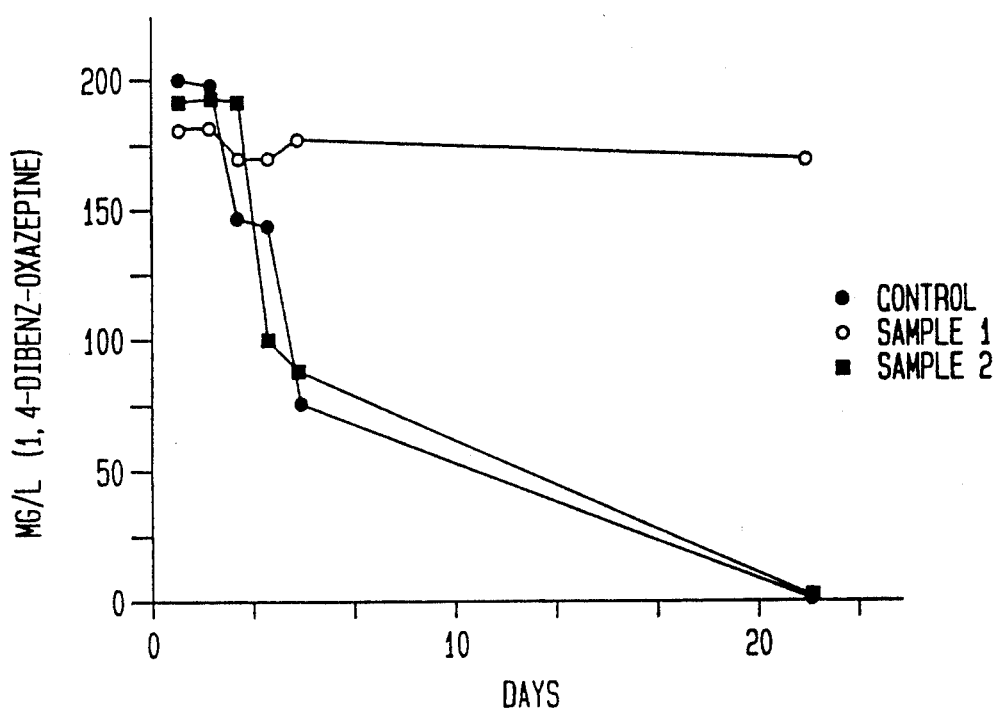
FIG. 1 is a graph illustrating the decreasing concentration of 1,4-dibenz-oxazepine as a function of time (days) in samples to which the bacteria CR-1 has been added.

The present invention relates to a method and compositions for biologically degrading 1,4-dibenz-oxazepine.

The degradation has been accomplished by contacting the 1,4-dibenz-oxazepine with a microorganism enzymatically capable of utilizing the 1,4-dibenz-oxazepine as a carbon source. The microorganism found to be useful is a strain of *Alcaligenes denitrificans denitrificans* (CR-1). A deposit of CR-1 has been made with the American Type Culture Collection as ATCC53957.

A proposed pathway for the 1,4-dibenz-oxazepine degradation has been postulated as the 1,4-dibenz-oxazepine being cleaved to form o-nitrophenol and O-cresol. The O-nitrophenol is believed to degrade to form catechol, which in turn is thought to oxidize via both ortho and meta positions to finally result in metabolically useful products such as acetyl-CoA succinate and formate acetaldehyde pyruvate. This portion of the proposed pathway is consistent with the observed degradation of O-nitrophenol and catechol. It was believed that O-cresol forms 3-methylcatechol which in turn has been degraded using CR-1. The mechanism is believed to be via meta fission to form acetate acetaldehyde pyruvate. The 1,4-dibenz-oxazepine and intermediates (except for o-cresol) in the proposed degradation pathway recited above have been observed to be degraded.

The strain of *Alcaligenes denitrificans denitrificans*, identified as CR-1, which is useful in the process of the present invention is resistant to concentrations of 1,4-dibenz-oxazepine up to at least 200 mg/L. CR-1 is capable of surviving in a aqueous environment, and more particularly in a aquatic ecosystem.

The CR-1 reduces 1,4-dibenz-oxazepine toxicity. The disappearance of 1,4-dibenz-oxazepine from cultures containing CR-1 evidences this reduction. The 1,4-dibenz-oxazepine is a carbon source for the CR-1. CR-1 was added to samples of the aquatic organisms *Daphnia magna* and the algae *Selenastrum capricornutum*. Degrading 1,4-dibenz-oxazepine reduced its toxicity to *Daphnia magna* and eliminated the toxicity to the algae. In fact, algal growth was stimulated indicating that some by-product of the 1,4-dibenz-oxazepine degradation was being used by the algae.

The present invention also includes compositions comprising the active microorganisms, preferably CR-1. Such compositions comprise CR-1 and a carrier, preferably in the form of a matrix material. The CR-1, and compositions comprising CR-1, are useful to degrade 1,4-dibenz-oxazepine in the environment and in bioreactors.

Preferably, the carrier is in the form of a matrix material. As used herein matrix material is a material useful for immobilization of the CR-1. Useful matrix materials include but are not limited to polymers such as polyacrylamide and non-polymeric materials which are preferably porous with diatomaceous earth preferred, particularly in pellet form such as those available from Manville Corp. of Denver, Colo. Useful methods for immobilization of the organism on the matrix and suitable matrix materials are available in the literature (see, for example, *Methods of Enzymology*, 44, 1976).

In accordance with a process to add CR-1 to a system comprising a compound selected from the group consisting of 1,4-dibenz-oxazepine, o-nitrophenol, catechol, and 3-methyl catechol and particularly containing 1,4-dibenz-oxazepine, the CR-1 is preferably used in an aqueous composition, wherein there is from about $1.0 \times 10^3$ to about $1.0 \times 10^8$, preferably from about $1.0 \times 10^4$ to about $1.0 \times 10^6$, and most preferably about $1.0 \times 10^5$ CR-1 cells/ml. The concentration is based on a ml of the composition. The system can be an environmental system such as an aquatic ecosystem or a bioreactor.

The composition can be added to the ecosystem in suitable form. Where the compound selected from the group consisting of 1,4-dibenz-oxazepine, o-nitrophenol, catechol and 3-methyl catechol is in an aquatic environment, the CR-1 is preferably added to the aquatic environment in an aqueous liquid composition. The composition is preferably added at ambient conditions which are typically from 15° to 40° C. The amount and concentration of CR-1 is based on the amount of the compound, i.e., 1,4-dibenz-oxazepine determined to be in the system. Preferably, the concentration of CR-1 is from about $1.0 \times 10^3$ to about $1 \times 10^8$ and more preferably from about $1.0 \times 10^4$ to about $1.0 \times 10^6$ cell/ml. The rate at which the 1,4-dibenz-oxazepine degrades will depend upon temperature, and the relative amounts of 1,4-dibenz-oxazepine and CR-1.

CR-1 can be used in a bioreactor for degrading a first composition comprising a compound selected from the group consisting of 1,4-dibenz-oxazepine, o-nitrophenol, catechol and 3-methyl catechol. The CR-1 is preferably used in an second composition comprising a carrier, in the form of a matrix material, wherein there is from about $1.0 \times 10^3$ to about $1.0 \times 10^8$, preferably about $1.0 \times 10^4$ to about $1.0 \times 10^6$, and more preferably about $1.0 \times 10^5$ CR-1 cells/ml.

In bioreactors for treating substances contaminated with 1,4-dibenz-oxazepine, the microorganism, preferably CR-1, is preferably used in a composition comprising a matrix material, preferably diatomaceous earth or a porous polymeric material. The composition is used in the form of a bed through which the 1,4-dibenz-oxazepine or a composition comprising 1,4-dibenz-oxazepine is fed. The matrix provides a physical confinement of the microorganism which permits its economical reuse. The temperature in the bioreactor can be ambient and is preferably from 15° to 40° C. and more preferably from 25° to 30° C. The feed stream containing the compound to be degraded, i.e., 1,4-dibenz-oxazepine is preferably maintained at a concentration of 1,4-dibenz-oxazepine of from 50 to 200 mg/L.

The examples set forth below illustrate the nature of the invention and the manner of carrying it out. However, the invention should not be considered as being limited to the details thereof.

PROCEDURES AND MATERIALS

The culture media used was T82MV which was obtained from the Standardized Aquatic Microcosm (SAM). SAM is a generic simulation of a freshwater community described by Taub and Real in *Standardized Aquatic Microcosm Protocol*, Contract No. 223-80-2352, Vol. II Food & Drug Administration, Washington, D.C. 1983, the text of which is hereby incorporated by reference.

Aquatic testing was done in accordance with American Society for Testing and Materials and Environmental Protection Agency guidelines. *Daphnia magna* were reared in the laboratory according to the procedures in Goulden, et.al., ASTM, *Special Technical Publication* 766, 1982, pp. 139–160, the text of which is hereby incorporated by reference.

The instrument conditions for The Perkin & Elmer High Performance Liquid Chromatagraph (HPLC) used were as follows:

Perkin & Elmer HPLC:
  Series 4 Liquid Chromatography Pump
  LC-85B Spectrophotometric Detector
  LC-Autocontrol
  LC-Terminal
  LC-100 Laboratory Integrator
  Wave Length: 210 nm
  Equilibrium Solvent: 60 percent $CH_3CN$
  Column: Perkin & Elmer $C_{18}$, Serial 2496, 15 cm
  Temperature: Room Temperature (22° C.)
  Flow Rate: 1 ml/min
  Attenuation: 128

The rates of degradation for a Compound Y were expressed in percentages and were calculated as follows:

$$\frac{\text{mg/L Compound } Y_{T1} - \text{mg/L Compound } Y_{T2}}{\text{mg/L/Compound } Y_{T1}} \times 100\%$$

T = time.

The area under the growth curve for determining toxicity reduction to *Selenastrum capricornutum* was calculated as follows:

$$A = \frac{(N_0 + N_1) - 2N_0}{2} \times (t_1) + \frac{(N_1 + N_2) - 2N_0}{2} \times$$

-continued
$$(t_2 - t_1) + \frac{(N_{n-1} + N_n)}{2} \times (t_n - t_{n-1})$$

Where:
  $N_0$ = number of cells at $t_0$
  $N_1$ = number of cells at $t_1$
  $N_n$ = number of cells at $t_n$
  $t_1$ = time of first measurement
  $t_n$ = time of the nth measurement.

The percent inhibition was calculated using A as determined above. The following equation was used:

$$\text{Percent in} = \frac{A_c - A_t}{A_c} \times 100\%$$

$A_c$ = Area under the growth curve for a control
$A_t$ = Area under the growth curve for a time t.

The VITEX Automated Microbial System is from McDonnell Douglas, Company. This system utilizes biochemical reagents and inhibitors to identify bacteria. If a color change is observed to occur, then the bacteria can utilize the chemical as a carbon source. All color changes are matched against an internal library on the system commuter.

The 96-Well Microplates from Biolog, Inc. contain 96 wells of premixed biochemical reagents used in identifying bacteria via carbon source utilization abilities.

The fatty acid analysis was performed by Microbial I.D., Inc using the Hewlett-Packard 5898A Microbial Identification System. HP5898A which is automated for using gas chromatography to analyze the lipid content in the bacterial cell wall. The lipid content is a map for identifying the bacteria. The map is then compared to an internally stored library in the system commuter.

EXAMPLE 1

12 gram bottom samples were taken from the mouth of Canal Creek in Aberdeen Proving Grounds, Md. The samples were placed in acid washed gallon glass jars with 1200 mls of T82MV media spiked with 20 mg/L 1,4-dibenz-oxazepine and the jars were placed in a chemical exhaust hood for 3 months. The hood was darkened to prevent the growth of algae.

At the end of 3 months two milliliter samples were withdrawn from the jars and plated onto nutrient agar spiked with 1,4-dibenz-oxazepine. After 90 days of replica-plating onto successively higher concentrations of 1,4-dibenz-oxazepine, an organism was thereby isolated which could resist 1,4-dibenz-oxazepine in concentrations up to 200 mg/L. It was given the designation CR-1. These isolated organisms were maintained in screw top culture tubes filled with 12 ml of axenic media containing 1.0 percent weight to volume protease peptone with 0.2 percent weight to volume yeast extract. Periodically, the organisms were serially diluted and placed on nutrient agar plates lacking 1,4-dibenz-oxazepine, incubated for 48 hours, and examined to ensure the presence of only a single species.

EXAMPLE 2

CR-1 was isolated using the procedure in Example 1. A 200 mg/L stock solution of 1,4-dibenz-oxazepine was prepared by using T82MV to dilute 100mg 1,4-dibenz-oxazepine dissolved in 20 ml 100 percent ethanol to a volume of 500 ml. The solution was then autoclaved, allowed to cool, and filtered through a 0.45 μm filter disk. The bacteria were then spun in a clinical centrifuge for 10 minutes (30×g) and the supernatant was discarded and replaced with 12 ml of T82MV. After 2 days, one ml (approximately 1×10⁵ cells) of the washed CR-1 was placed into 100 ml of T82MV spiked with 200 mg/L 1,4-dibenz-oxazepine.

Five milliliter samples were withdrawn at 24 hour intervals and filtered through a 0.45 μm filter disk. Ten microliters of this filtrate was then injected into a Perkin & Elmer HPLC in order to detect the levels of 1,4-dibenz-oxazepine present. A control sample was also injected into the HPLC.

FIG. 1 shows the degradation results for two 10 microliter samples of the filtrate and a control. The concentration of 1,4-dibenz-oxazepine (mg/l) present in the sample was measured and recorded as a function of time (days). The figure includes the first two days prior to the addition of the 1,4-dibenz-oxazepine.

EXAMPLE 3

The same procedures were followed as in Example 2 with one exception, the HPLC was used to measure the levels of 1,4-dibenz-oxazepine as well as levels of its proposed degradation products O-Nitrophenol, O-Cresol, catachol, and 3-methyl catachol present in the sample. The percent degradation for each of these compounds was then determined as follows:

| Compound | % Degradation/24 hrs. |
|---|---|
| 1,4-dibenz-oxazepine | 24.0 |
| 0-nitrophenol | 35.6 |
| 3-methylcatachol | 21.0 |
| catechol | 3.4 |
| o-cresol | 0.0 |

The microorganisms were identified as *Alcaligenes denitrificans denitrificans* by using the methods in the following 3 examples:

EXAMPLE 4

CR-1 was grown on chocolate agar over night for approximately 18 hours. A sample was gram stained with crystal violet and identified as a gram negative species. A single colony of approximately 3 mm diameter was then suspended in sterile saline solution composed of 1.8 ml 0.5% NaCl and agitated to form a uniform suspension. A sterile transfer stick was used to load a sample of the bacteria on to a VITEX Automated Microbial System gram negative identification card. The card was sealed and placed into the VITEX reader/incubator tray and incubated for 18 hours. It was then automatically read in the VITEX optical unit. A color indicator was used to identify positive reactions and the computer then ran through an internally stored library and selected the most likely match.

EXAMPLE 5

A biolog 96 Well Plate was used to identify the bacteria via its ability to use various carbon sources. CR-1 was grown on nutrient agar plates for approximately 18 hours. Cells were scraped off the agar plate and placed into sterile 0.85% NaCl. The optical density of the suspension was determined at a wave length of 590 nm. 150 μl of the cell suspension was placed in each of the 96 wells of the plate and placed in an incubator for 24 hours at 28° C. In the wells that respiration occurred, tetrazolium dye was reduced to form a purple color.

EXAMPLE 6

CR-1 was grown for 24 hours at 28° C. on trypticase soy broth agar which contains 30 grams trypticase and 15 grams bacto agar in 1L distilled water. The bacteria cells were harvested and prepared for analysis. The cell suspension was run on gas chromatography to separate fatty acids and the computer compared the fatty acid profile to an internal library of over 6,000 known strains of gram negative bacteria and gave the most likely match.

EXAMPLE 7

The identification of CR-1 as *Alcaligenes denitrificans denitrificans* by the methods used in Examples 4, 5, and 6 was substantiated by electron microscopy. CR-1 was centrifuged at 375×g for 10 minutes at 4° C. The resultant pellet was fixed via primary fixation for 45 minutes in approximately one part sample to 10 parts 1.6% formaldehyde and 2.5% glutaraldehyde in 0.05M sodium cacodylate. The pellet was washed 3 times for 10 minutes at the conditions described above. Following the wash, the bacteria were post fixed for 1 hour in buffered 1% osmium tetroxide, dehydrated in graded ethanols (50, 70, 95, and 100%) and recentrifuged to minimize cell losses and repellet the sample. The bacteria were then embedded in epoxy resin, ultrathin sections cut and then counterstained with uranyl acetate and lead citrate. The sections were examined by the microscope.

EXAMPLE 8

*Daphnia magna* were exposed to a concentration of approximately 1.0×10⁵ CR-1 cells/ml. Daphnia were observed at 24 and 48 hours. Microscopic observations were made to see if the bacteria were filtered and ingested by the daphnia during the exposure period. The daphnia showed no toxic or adverse effects from exposure to the bacteria.

EXAMPLE 9

A 20 mg/L stock solution of 1,4-dibenz-oxazepine was prepared as in Example 2 but without addition of ethanol solvent. The stock was divided into two separate containers, autoclaved, and filtered. To one container, approximately 1.0×10⁵ CR-1 cells/ml were added. Both containers were incubated for six days at 30° C.

*Daphnia magna* were reared in the laboratory. Daphnid stock cultures were fed a mixture of *Ankistrodesmus falcatus, Selenastrum capricornutum* and *Chlamydomonas reinhardi* 90. The culture media was prepared from municipal drinking water that was hardened to 132 ppm total $CaCO_3$. The pH was adjusted to 7.2-7.5. Ten *Daphnia magna* neonates of less than 24 hours old were placed into 250 ml glass beakers filled with 100 ml of the stock solution. The test beakers were placed into an incubator with a light-dark cycle of 16:8 hrs with 315 ft. candles of light, at a temperature of 20° C. Two replicates were used in each test. Daphnia were gently touched with a pasteur pipet at 24 and 48 hours. If the daphnia could not swim actively for 15 seconds immobilization was recorded. The effective concentration at which 50 percent of the organisms are immobilized ($EC_{50}$) was computed.

Figure 2:
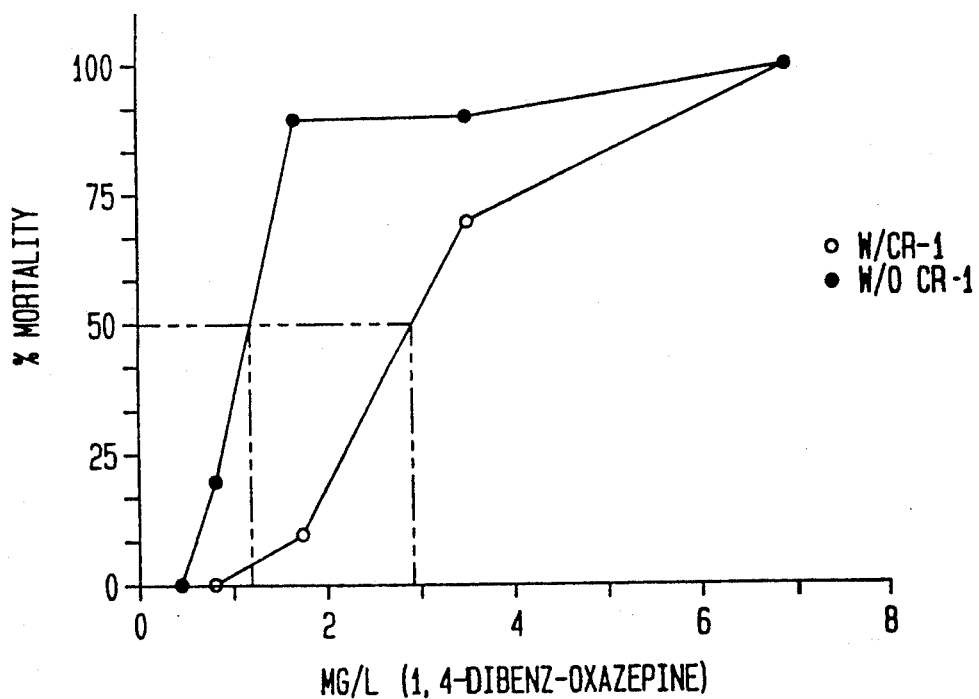
FIG. 2 is a graph illustrating the toxicity of 1,4-dibenz-oxazepine to *Daphnia magna* with and without the addition of CR-1 measured by the percentage of Daphnia mortality as a function of mg/L 1,4-dibenz-oxazepine concentration.

FIG. 2 represents the percent mortality values plotted against 1,4-dibenz-oxazepine concentration (mg/l) at 48 hours. The 48 hour EC50 for Daphnia samples without CR-1 was determined to be 1.05 mg/l. The 48 hour EC50 for samples with CR-1 was determined to be 2.8 mg/l.

EXAMPLE 10

Figure 3:
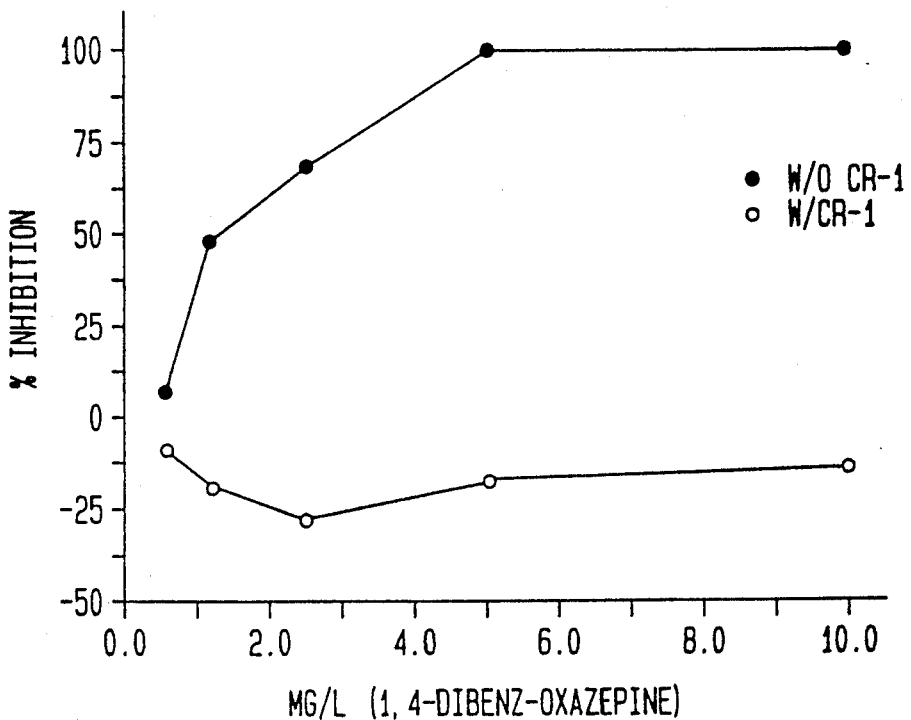
FIG. 3 is a graph of the percent inhibition in growth to *Selenastrum capricornutum* observed as a function of 1,4-dibenz-oxazepine concentration in samples with and without CR-1.
Figure 4:
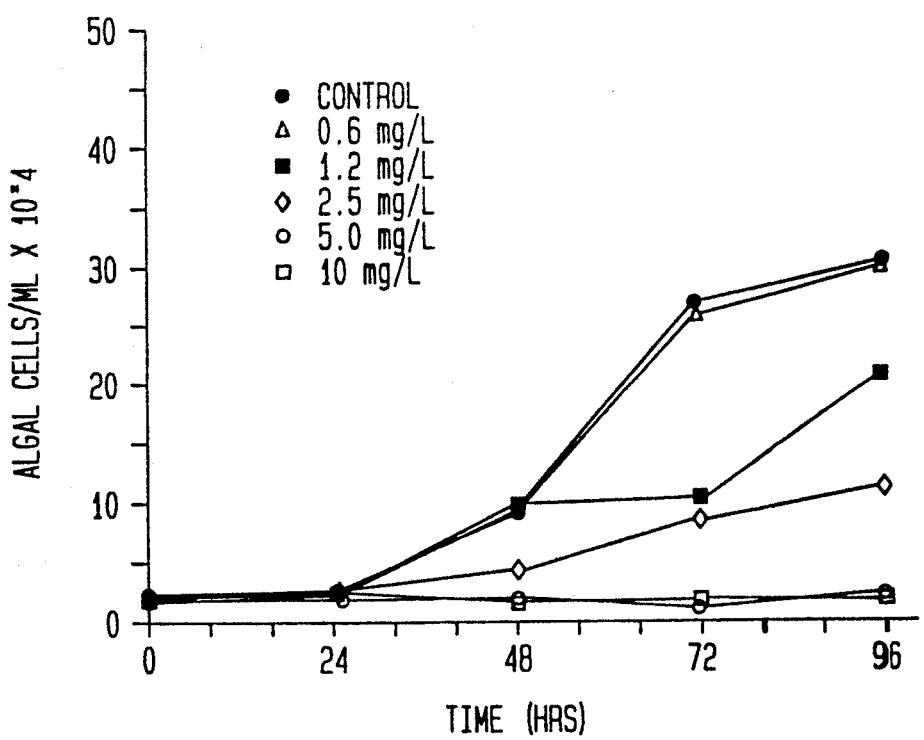
FIG. 4 is a graph of the toxicity of 1,4-dibenz-oxazepine to *Selenastrum capricornutum* (algal cells/ml × $10^4$) recorded as a function of time (hours).
Figure 5:
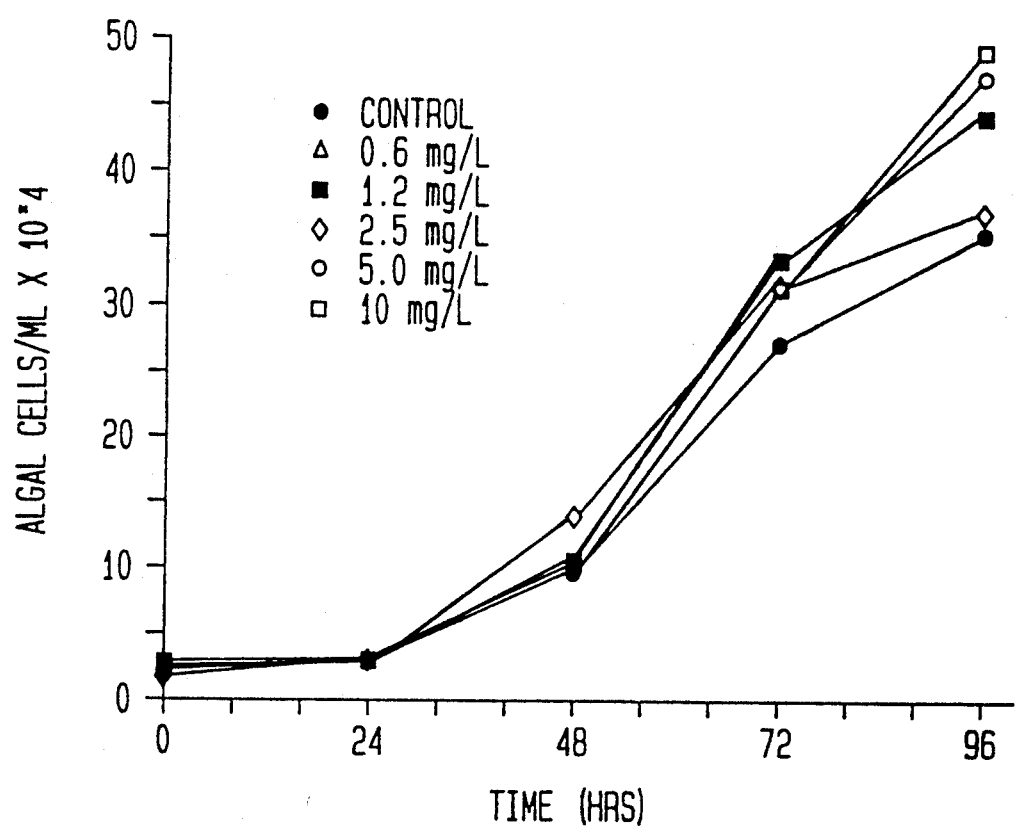
FIG. 5 is a graph of the reduction in toxicity observed with the addition of CR-1 to the algae *Selenastrum capricornutum* (algal cells/ml × $10^4$) as a function of time (hours).

Stock cultures of *Selenastrum capricornutum* were maintained on 1.5 percent by weight Difco-Bacto agar slants. Test algae were grown in a semi-flow through culture apparatus on T82MV and taken during log phase growth for inoculation into the test chambers. Five hundred ml Erlenmeyer flasks with ground glass stoppers were used as test chambers. One hundred mls of T82MV media were placed in each test chamber and innoculated with approximately $4.0 \times 10^4$ algal cells per ml. The algae were placed in an incubator under the same conditions as described in Example 7 for the daphnia 48 hour assays. Using a Newbauer Counting Chamber, cell densities were determined every 24 hours for five consecutive days. The area under the growth curve was calculated and the percent inhibition was then determined using the value discerned for the area. The percent inhibition as a function of 1,4-dibenz-oxazepine concentration for a sample with CR-1 and without CR-1 are represented in FIG. 3. The concentration at which algal growth is reduced to 50 percent of the control ($IC_{50}$) was determined at 96 hours to be 1.45 mg/L. After 10 days, no toxicity to the algae was observed. The toxicity to 1,4-dibenz-oxazepine was indicated by a reduction in the number of algae cells *Selenastrum capricornutum* and is recorded as a function of time (hrs.) in FIG. 4. The reduction in toxicity with the addition of CR-1 to the algae was recorded in FIG. 5 as a function of time (hrs.).

While exemplary embodiments of the invention have been described, the true scope of the invention is to be determined from the following claims.

What is claimed is:

1. A composition comprising a strain of a biological pure culture of *Alcaligenes denitrificans denitrificans* having an American Type Culture Collection No. 53957, and a porous carrier.

2. The composition according to claim 1 where the carrier is selected from the group consisting of particulate proteins and porous polymers.

3. The composition according to claim 1 where the carrier is a support bed of autoclavable diatomaceous earth.

* * * * *